(12) United States Patent
Hong et al.

(10) Patent No.: US 9,351,785 B2
(45) Date of Patent: May 31, 2016

(54) MEDICAL TREATMENT DEVICES HAVING ADJUSTABLE LENGTH AND/OR DIAMETER

(71) Applicant: Covidien LP, Mansfield, MA (US)

(72) Inventors: Chunlang Hong, Shanghai (CN); Li Wang, Shanghai (CN); Jiun Keat Ong, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/498,364

(22) Filed: Sep. 26, 2014

(65) Prior Publication Data
US 2015/0094704 A1    Apr. 2, 2015

(30) Foreign Application Priority Data
Sep. 29, 2013 (CN) ................. PCT/CN2013/084574

(51) Int. Cl.
*A61B 18/12* (2006.01)
*A61B 18/08* (2006.01)
*A61B 18/10* (2006.01)
A61B 18/00 (2006.01)

(52) U.S. Cl.
CPC .............. *A61B 18/082* (2013.01); *A61B 18/10* (2013.01); *A61B 2018/00577* (2013.01); *A61B 2018/00702* (2013.01); *A61B 2018/00827* (2013.01); *A61B 2018/00875* (2013.01)

(58) Field of Classification Search
CPC ............... A61B 18/082; A61B 18/10; A61B 2018/00577; A61B 2018/00702; A61B 2018/00827; A61B 2018/00875
See application file for complete search history.

(56) References Cited

U.S. PATENT DOCUMENTS

| 5,492,529 | A * | 2/1996 | Neuwirth et al. ............. 607/143 |
| 6,447,508 | B1 | 9/2002 | Sharkey et al. |
| 6,517,534 | B1 | 2/2003 | McGovern et al. |
| 6,743,226 | B2 | 6/2004 | Cosman et al. |
| 6,949,097 | B2 | 9/2005 | Stewart et al. |
| 8,043,285 | B2 | 10/2011 | Thompson et al. |
| 2004/0127963 | A1 | 7/2004 | Uchida et al. |
| 2006/0095103 | A1 | 5/2006 | Eggers et al. |
| 2008/0221650 | A1 | 9/2008 | Turner et al. |
| 2009/0125018 | A1 | 5/2009 | Merrick et al. |
| 2010/0106150 | A1 | 4/2010 | Thompson et al. |
| 2010/0318081 | A1 | 12/2010 | Sato et al. |
| 2011/0238055 | A1 | 9/2011 | Kim et al. |

FOREIGN PATENT DOCUMENTS

| CN | 1895183 | 1/2007 |
| WO | WO 99/49932 | 10/1999 |

OTHER PUBLICATIONS

Extended Search Report from counterpart European Patent Application No. 14186193.0, dated Jan. 19, 2015, 6 pp.

(Continued)

*Primary Examiner* — Michael Peffley
*Assistant Examiner* — Daniel Fowler

(57) ABSTRACT

The present embodiments enable the length and/or diameter of the heating segment of a medical treatment device to be adjusted on the fly during a treatment procedure, without a need to interrupt the procedure, thus allowing a single catheter to be used at different locations in a hollow anatomical structure.

8 Claims, 16 Drawing Sheets

(56) References Cited

OTHER PUBLICATIONS

International Search Report and Written Opinion on related PCT Application No. PCT/CN2013/084574 from International Searching Authority (SIPO) dated Jul. 3, 2014.

First Office Action, and translation thereof, from counterpart Chinese Patent Application No. 201410513084.9, dated Mar. 17, 2016, 16 pp.

* cited by examiner

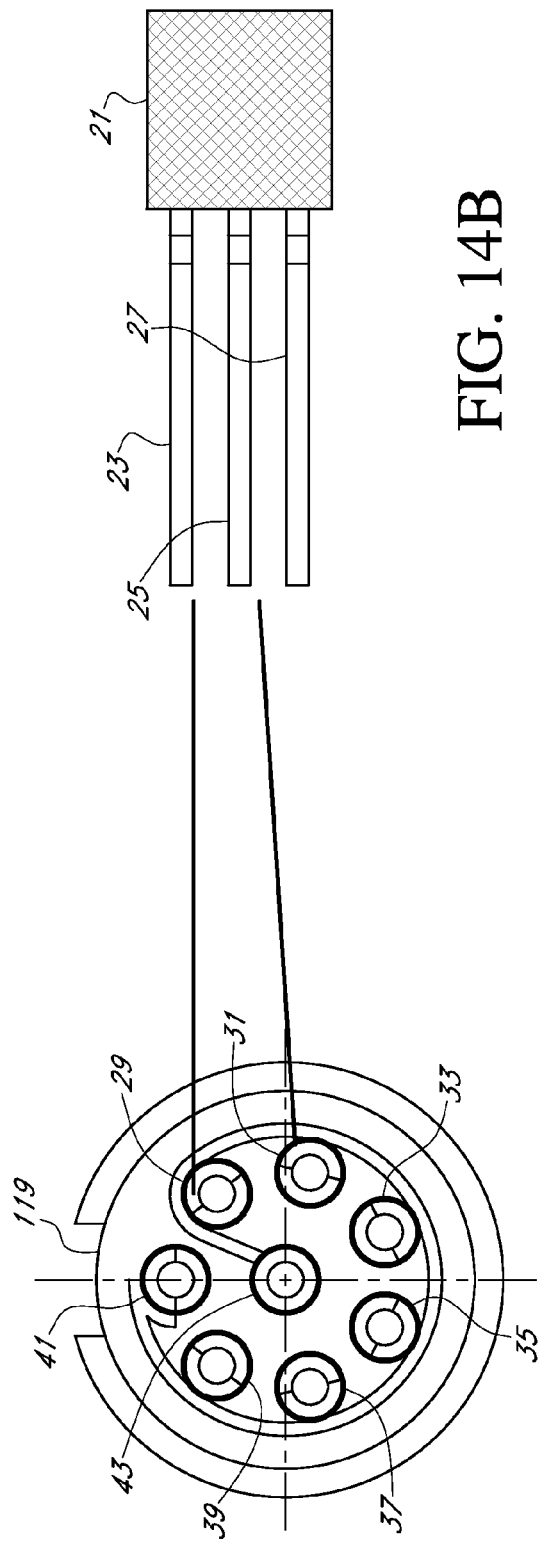

MEDICAL TREATMENT DEVICES HAVING ADJUSTABLE LENGTH AND/OR DIAMETER

CROSS-REFERENCE TO RELATED APPLICATIONS

The present application claims the benefit of priority under 35 U.S.C. 119 of PCT/CN2013/084574, filed Sep. 29, 2013, the contents of which are hereby incorporated by reference herein.

TECHNICAL FIELD

The present embodiments relate to medical treatment devices, particularly medical treatment devices having adjustable length and/or diameter.

BACKGROUND

Various endovenous treatments are commonly used for treating venous reflux disease, and other diseases of hollow anatomical structures (HAS). Venous reflux disease is a disease caused by damaged vein valves, which typically prevent blood from flowing backwards in a vein. Thus, with damaged valves, particularly in the legs, gravity works against the blood flowing upward toward the heart, resulting in venous congestion and varicose veins. Varicose veins typically happen in superficial veins, such as the Greater Saphenous Vein (GSV) and the Lesser Saphenous Vein (LSV), creating unsightly and painful bulges and tortuous veins, and may lead to many serious complications.

Electrosurgical heating is one endovenous treatment for venous reflux disease, as well as other diseases in HAS. Electrosurgical heating may use radio frequency current to apply energy to create targeted tissue ablation to seal off damaged veins. Electrosurgical equipment typically includes a generator, such as an RF generator, and a catheter having a heating segment located at the distal end, which is inserted into the vein(s) during treatment. The heating segment may use RF energy driven by the RF generator to heat and seal the vein. Currently, the catheters include a heating segment having a fixed length, such as 7 cm, 4 cm, 3 cm, and a specific combination of length and diameter, for example, 7F on a 7 cm catheter, 5F on a 3 cm catheter, or 3F on a 1 cm catheter. (F indicates the French scale for measuring the outside diameter of a catheter, 1F=0.33 mm.)

However, the Saphenous Vein length and diameter varies at the thigh, calf and ankle portions and from patient to patient. For example, the Greater Saphenous Vein may range in diameter from about 2.5 to 14.0 mm at the femoral junction, 1.5 to 12.0 mm in the thigh, and 1.0 to 8.0 mm in the calf, while Lesser Saphenous Vein diameters may range from 1.5 to 3.0 mm. Often, there may be a need for treating these various sizes in a single patient in a single procedure.

SUMMARY

The various embodiments of the present medical treatment devices having adjustable length and/or diameter have several features. Without limiting the scope of the present embodiments as expressed by the claims that follow, their features now will be discussed briefly. After considering this discussion, and particularly after reading the section entitled "Detailed Description," one will understand how the features of the present embodiments provide the advantages described herein.

One of the present embodiments comprises an adjustable-dimension catheter for tissue ablation. The catheter comprises an elongate shaft having a distal end and a proximal end. The catheter further comprises a shaft connector adjacent the distal end of the shaft, the shaft connector having a plurality of shaft electrical contacts. The catheter further comprises a first heating assembly having a first heating element having a first length and a first diameter at a distal end thereof, and a first heating element connector adjacent a proximal end thereof, the first heating element connector having a plurality of first heating element electrical contacts having a first heating element electrical contact configuration. The catheter further comprises a second heating assembly having a second heating element having a second length and a second diameter at a distal end thereof, and a second heating element connector adjacent a proximal end thereof, the second heating element connector having a plurality of second heating element electrical contacts having a second heating element electrical contact configuration. The first and second heating element connectors are selectively connectable to the shaft connector at the distal end of the shaft to selectively couple the first and second heating assemblies to the shaft. At least one of the first and second lengths and the first and second diameters of the first and second heating elements are different. The first and second heating element electrical contact configurations are different, such that the first heating element electrical contacts contact a first combination of the shaft electrical contacts of the shaft connector when the first heating element connector is connected to the shaft connector, and the second heating element electrical contacts contact a second combination of the shaft electrical contacts of the shaft connector when the second heating element connector is connected to the shaft connector, and the first and second combinations of the shaft electrical contacts are different.

The shaft electrical contacts and the first and second heating element electrical contacts may have a stepped configuration in which the contacts are spaced in the axial direction and at least two of the contacts are spaced in the radial direction.

The heating elements may comprise an electrically resistive element.

The electrically resistive element may be a coil.

The catheter may further comprise an indicator adjacent a proximal end of the shaft that indicates which of the first and second heating elements is connected to the shaft.

Another of the present embodiments comprises an adjustable-dimension catheter for tissue ablation. The catheter comprises an elongate shaft having a distal end and a proximal end. The catheter further comprises a shaft connector adjacent the distal end of the shaft, the shaft connector having a plurality of shaft electrical contacts. The catheter further comprises a plurality of heating assemblies, each comprising a heating element of a different length at a distal end thereof, and each having a heating element connector adjacent a proximal end thereof, each of the heating element connectors having a plurality of heating element electrical contacts. The heating element connectors are selectively connectable to the shaft connector at the distal end of the shaft to selectively couple the heating assemblies to the shaft. The heating element electrical contacts on each of the heating assemblies have different configurations, such that the heating element electrical contacts on each of the heating assemblies contact a different combination of the shaft electrical contacts of the shaft connector depending on a length of a given one of the heating elements.

The catheter may further comprise a power source configured to automatically detect a length of a connected one of the heating elements and adjust a level of power delivery for a desired energy output.

The shaft electrical contacts and the heating element electrical contacts may have a stepped configuration in which the contacts are spaced in the axial direction and at least two of the contacts are spaced in the radial direction.

The catheter may further comprise a first set of screw threads on the shaft connector and mating second sets of screw threads on the heating element connectors.

The heating elements may comprise at least one radio frequency (RF) electrode.

The heating elements may comprise an electrically resistive element.

The heating elements may each comprise a different diameter.

The catheter may further comprise an indicator adjacent a proximal end of the shaft that indicates which of the heating elements is connected to the shaft.

The indicator may comprise at least one light-emitting diode (LED).

The indicator may comprise a plurality of differently colored LEDs.

Another of the present embodiments comprises a set of heating assemblies configured to be secured to a catheter. The set of heating assemblies comprises at least a first heating assembly having a first heating element of a first length and a first diameter at a distal end thereof, and a first heating element connector adjacent a proximal end thereof, the first heating element connector having a plurality of first heating element electrical contacts having a first heating element electrical contact configuration. The set of heating assemblies further comprises at least a second heating assembly having a second heating element of a second length and a second diameter at a distal end thereof, and a second heating element connector adjacent a proximal end thereof, the second heating element connector having a plurality of second heating element electrical contacts having a second heating element electrical contact configuration. The first and second heating element connectors are selectively connectable to a shaft connector at a distal end of the catheter to selectively couple the first and second heating assemblies to the shaft. At least one of the first and second lengths and the first and second diameters of the first and second heating elements are different.

The first and second heating element electrical contacts may have a stepped configuration in which the contacts are spaced in the axial direction and at least of the two contacts are spaced in the radial direction.

The heating elements may comprise an electrically resistive element.

The electrically resistive element may be a coil.

The set of heating assemblies may further comprise a first set of screw threads on the first heating assembly a second set of screw threads on the second heating assembly.

Another of the present embodiments comprises a method for tissue ablation. The method comprises connecting a first heating element having a first length and a first diameter to a distal end of an elongate shaft. The method further comprises ablating tissue with the first heating element. The method further comprises disconnecting the first heating element from the shaft. The method further comprises connecting a second heating element having a second length and a second diameter to the distal end of the shaft, wherein the first and second lengths and the first and second diameters are different. The method further comprises ablating tissue with the second heating element. When the first heating element is connected to the shaft, heating element electrical contacts on the first heating element contact a first combination of shaft electrical contacts on the shaft, and when the second heating element is connected to the shaft, heating element electrical contacts on the second heating element contact a second combination of the shaft electrical contacts on the shaft.

When either of the heating elements is connected to the shaft, a power source may automatically detect at least one of a length and a diameter of the connected one of the heating elements and adjust a level of power delivery for a desired energy output.

The shaft and heating element electrical contacts may have a stepped configuration in which the contacts are spaced in the axial direction and also in the radial direction.

Connecting the heating elements to the distal end of the shaft may comprise connecting a first set of screw threads on the distal end of the shaft to second sets of screw threads on the heating elements.

The heating elements may comprise at least one radio frequency (RF) electrode.

The heating elements may comprise an electrically resistive element.

The electrically resistive element may be a coil.

The method may further comprise indicating which of the heating elements is connected to the shaft via an indicator adjacent a proximal end of the shaft.

The indicator may comprise at least one light-emitting diode (LED).

Another of the present embodiments comprises a method for tissue ablation. The method comprises connecting a first heating segment having a first length and a first diameter to a distal end of an elongate shaft. The method further comprises ablating tissue with the first heating segment. The method further comprises disconnecting the first heating segment from the shaft. The method further comprises connecting a second heating segment having a second length and a second diameter to a distal end of the shaft, wherein the first and second lengths and the first and second diameters are different. The method further comprises ablating tissue with the second heating segment. When the first heating segment is coupled to the shaft, the heating segment electrical contacts of the first heating segment are electrically connected to one of a plurality of different combinations of the shaft electrical contacts depending on a length of the first heating segment.

When either of the first and second heating segments is connected to the shaft, a power source may automatically detect at least one of a length and a diameter of the connected one of the heating segments and adjust a level of power delivery for a desired energy output based on the detected length.

The shaft and heating segment electrical contacts may have a stepped configuration in which the contacts are spaced in the axial direction and also in the radial direction.

Connecting the first and second heating segments to the distal end of the shaft may comprise connecting a first set of screw threads on the distal end of the shaft to second sets of screw threads on the heating segments.

The heating segments may comprise at least one radio frequency (RF) electrode.

The heating segments may comprise an electrically resistive element.

The method may further comprise indicating which of the heating segments is connected to the shaft via an indicator adjacent a proximal end of the shaft.

The indicator may comprise at least one light-emitting diode (LED).

Another of the present embodiments comprises a medical treatment device having an adjustable treatment diameter. The device comprises a catheter having an elongate flexible shaft with a proximal end and a distal end. The device further comprises a first electrically resistive heating element disposed at the distal end of the shaft, the first electrically resistive heating element having a first outer diameter. The device further comprises first electrical contacts on the catheter shaft. The device further comprises a second electrically resistive heating element having a second, larger, outer diameter and connectable to the shaft to at least partially surround the first electrically resistive heating element, the second electrically resistive heating element having second electrical contacts connectable to the first electrical contacts.

The first and second electrically resistive heating elements may be coils.

The device may be in combination with a power source, wherein the power source is configured to automatically detect whether the second electrical contacts are connected to the first electrical contacts and adjust an energy output to the second heating element to a desired energy output.

Detecting whether the second electrical contacts are connected may comprise measuring at least one of a resistance value and an inductance value of the second heating element by passing a detecting current through the second heating element.

The second heating element may be connectable to the distal end of the shaft by one of a screw joint, or a latch joint.

Another of the present embodiments comprises a medical treatment device having an adjustable treatment diameter. The device comprises a catheter having an elongate flexible shaft with a proximal end and a distal end. The device further comprises a first heating element disposed at the distal end of the shaft, the first heating element having a first outer diameter. The device further comprises first electrical contacts on the catheter shaft. The device further comprises a second heating element having second electrical contacts connectable to the first electrical contacts, the second heating element having a second outer diameter that is greater than the first outer diameter.

When the second electrical contacts are connected to the first electrical contacts the second heating element may at least partially surround the first heating element.

The device may be in combination with a power source, wherein the power source is configured to automatically detect whether the second electrical contacts are connected to the first electrical contacts and adjust an energy output to the second heating element to a desired energy output.

Detecting whether the second electrical contacts are connected may comprise measuring at least one of a resistance value and an inductance value of the second heating element by passing a detecting current through the second heating element.

The second heating element may be connectable to the distal end of the shaft by one of a screw joint, or a latch joint.

The device may further comprise a third heating element having third electrical contacts connectable to the first electrical contacts, the third heating element having a third outer diameter that is greater than the second outer diameter.

Another of the present embodiments comprises a medical treatment device having an adjustable treatment diameter. The device comprises a catheter having an elongate flexible shaft with a proximal end and a distal end. The device further comprises a first heating element disposed at the distal end of the shaft, the first heating element having a first outer diameter. The device further comprises a second heating element connectable to the distal end of the shaft over the first heating element, the second heating element having a second outer diameter that is greater than the first outer diameter.

The device may be in combination with a power source, wherein the power source is configured to automatically detect whether the second heating element is connected to the distal end of the shaft and adjust an energy output to the second heating element to a desired energy output.

Detecting whether the second heating element is connected may comprise measuring at least one of a resistance value and an inductance value of the second heating element by passing a detecting current through the second heating element.

The device may further comprise electrical contacts on the shaft, the electrical contacts configured to electrically connect the second heating element to a power source.

The power source may be configured to automatically detect whether the second heating element is connected to the electrical contacts and adjust an energy output to the second heating element to a desired energy output.

Detecting whether the second heating element is connected to the electrical contacts may comprise detecting whether a detecting current is flowing between the electrical contacts.

Detecting whether the second heating element is connected to the electrical contacts may comprise measuring at least one of a resistance value and an inductance value of the second heating element by passing a detecting current through the second heating element.

The second heating element may be connectable to the distal end of the shaft by one of a screw joint, or a latch joint.

The device may further comprise a third heating element connectable to the distal end of the shaft over the first heating element, the third heating element having a third outer diameter that is greater than the second outer diameter.

The second heating element may comprise an inner diameter greater than or equal to the first outer diameter of the first heating element.

Another of the present embodiments comprises a method for tissue ablation. The method comprises positioning a first heating element adjacent to a target tissue, the first heating element disposed at a distal end of an elongate shaft, wherein the elongate shaft includes a proximal end and the distal end, and the first heating element having a first outer diameter. The method further comprises ablating the target tissue with the first heating element. The method further comprises connecting a second heating element to the distal end of the shaft over the first heating element, the second heating element having a second outer diameter that is greater than the first outer diameter. The method further comprises ablating a second target tissue with the second heating element.

The method may further comprise detecting with a power source connected to the proximal end of the shaft whether the second heating element is connected to the shaft and adjusting an energy output to a desired energy output.

Detecting whether the second heating element is connected may comprise measuring at least one of a resistance value and an inductance value of the second heating element by passing a small current through the second heating element.

The method may further comprise disconnecting the second heating element from the shaft and connecting a third heating element to the shaft, the third heating element having a third outer diameter that is greater than the second outer diameter.

Another of the present embodiments comprises a tissue treatment device. The device comprises an elongate shaft having a distal end. The device further comprises a heating element disposed at the distal end of the shaft, the heating element having a proximal end and a distal end. The device further comprises a first electrical pathway configured to extend between a power source, the proximal end of the heating element, and the distal end of the heating element, and defining a first treatment length extending between the proximal and distal ends of the heating element. The device further comprises a second electrical pathway configured to extend between the power source, the distal end of the heating element, and an intermediate point along the heating element intermediate the proximal and distal ends thereof, and defining a second treatment length extending between the intermediate point and the distal end of the heating element.

The device may further comprise a switch configured for selection of power delivery to the first electrical pathway or the second electrical pathway.

The power source may be configured to automatically distinguish between the first and second treatment lengths and adjust a level of power delivery for a desired energy output.

The heating element may be an electrically resistive heating element.

The heating element may be an electrically resistive coil.

Another of the present embodiments comprises a tissue treatment device. The device comprises an elongate shaft having a distal end. The device further comprises a heating element disposed at the distal end of the shaft, the heating element having a proximal end and a distal end. The device further comprises a first electrical pathway configured to extend between a power source, the proximal end of the heating element, and the distal end of the heating element, and defining a first treatment length extending between the proximal and distal ends of the heating element. The device further comprises a second electrical pathway configured to extend between the power source, the proximal end of the heating element, and an intermediate point along the heating element between the proximal and distal ends thereof, and defining a second treatment length extending between the intermediate point and the proximal end of the heating element.

The device may further comprise a switch configured for selection of power delivery to the first electrical pathway or the second electrical pathway.

The power source may be configured to automatically distinguish between the first and second treatment lengths and adjust a level of power delivery for a desired energy output.

The heating element may be an electrically resistive heating element.

The heating element may be an electrically resistive coil.

Another of the present embodiments comprises a method for tissue treatment. The method comprises positioning a catheter having an elongate shaft with a heating element disposed at a distal end thereof such that the heating element is adjacent a first treatment site in a hollow anatomical structure (HAS). The method further comprises delivering power during a first power delivery phase from a power source connected to the heating element along a first electrical pathway extending between the power source, a proximal end of the heating element, and a distal end of the heating element, thereby defining a first treatment length between the distal and proximal ends of the heating element. The method further comprises moving the catheter along the HAS such that the heating element is adjacent a second treatment site in the HAS. The method further comprises delivering power during a second power delivery phase from the power source along a second electrical pathway extending between the power source, a distal end of the heating element, and an intermediate point along the heating element intermediate the proximal and distal ends thereof, thereby defining a second treatment length between the intermediate point and the distal end of the heating element.

Delivering power during the second power delivery phase may comprise switching power delivery from the first electrical pathway to the second electrical pathway.

The power source may be configured to automatically distinguish between the first and second treatment lengths and adjust a level of power delivery for a desired energy output.

The heating element may be an electrically resistive heating element.

The heating element may be an electrically resistive coil.

Another of the present embodiments comprises a method for tissue ablation. The method comprises positioning a catheter having an elongate shaft with a heating element disposed at a distal end thereof such that the heating element is adjacent a first treatment site in a hollow anatomical structure (HAS). The method further comprises delivering power during a first power delivery phase from a power source connected to the heating element along a first electrical pathway extending between the power source, a proximal end of the heating element, and a distal end of the heating element, thereby defining a first treatment length between the distal and proximal ends of the heating element. The method further comprises moving the catheter along the HAS such that the heating element is adjacent a second treatment site in the HAS. The method further comprises delivering power during a second power delivery phase from the power source along a second electrical pathway extending between the power source, a proximal end of the heating element, and an intermediate point along the heating element intermediate the proximal and distal ends thereof thereby defining a second treatment length between the intermediate point and the proximal end of the heating element.

Delivering power during the second power delivery phase may comprise switching power delivery from the first electrical pathway to the second electrical pathway.

The power source may be configured to automatically distinguish between the first and second treatment lengths and adjust a level of power delivery for a desired energy output.

The heating element may be an electrically resistive heating element.

The heating element may be an electrically resistive coil.

Another of the present embodiments comprises a method of varying a treatment length of a heating element disposed at a distal end of a tissue treatment device. The method comprises delivering power to the heating element during a first power delivery phase, wherein the power is delivered from a power source along a first electrical pathway extending between the power source, a proximal end of the heating element, and a distal end of the heating element, thereby defining a first treatment length between the distal and proximal ends of the heating element. The method further comprises delivering power to the heating element during a second power delivery phase wherein the power is delivered from the power source along a second electrical pathway extending between the power source, a distal end of the heating element, and an intermediate point along the heating element intermediate the proximal and distal ends thereof, thereby defining a second treatment length between the intermediate point and the distal end of the heating element.

Delivering power during the second power delivery phase may comprise switching power delivery from the first electrical pathway to the second electrical pathway.

The power source may be configured to automatically distinguish between the first and second treatment lengths and adjust a level of power delivery for a desired energy output.

The heating element may be an electrically resistive heating element.

The heating element may be an electrically resistive coil.

Another of the present embodiments comprises a method of varying a treatment length of a heating element disposed at a distal end of a tissue treatment device. The method comprises delivering power to the heating element during a first power delivery phase, wherein the power is delivered from a power source along a first electrical pathway extending between the power source, a proximal end of the heating element, and a distal end of the heating element, thereby defining a first treatment length between the distal and proximal ends of the heating element. The method further comprises delivering power to the heating element during a second power delivery phase wherein the power is delivered from the power source along a second electrical pathway extending between the power source, a proximal end of the heating element, and an intermediate point along the heating element intermediate the proximal and distal ends thereof, thereby defining a second treatment length between the intermediate point and the proximal end of the heating element.

Delivering power during the second power delivery phase may comprise switching power delivery from the first electrical pathway to the second electrical pathway.

The power source may be configured to automatically distinguish between the first and second treatment lengths and adjust a level of power delivery for a desired energy output.

The heating element may be an electrically resistive heating element.

The heating element may be an electrically resistive coil.

The present embodiments enable the length and/or diameter of the heating segment of a medical treatment device to be adjusted on the fly during a treatment procedure, without a need to interrupt the procedure. Such adjustability enables a single catheter to be used at different locations in a hollow anatomical structure (HAS) where the length and/or diameter of a portion of the HAS to be treated may vary.

BRIEF DESCRIPTION OF THE DRAWINGS

The various embodiments of the present medical treatment devices having adjustable length and/or diameter now will be discussed in detail with an emphasis on highlighting the advantageous features. These embodiments are for illustrative purposes only. These drawings include the following figures, in which like numerals indicate like parts:

FIG. 14A is a front elevation view of one embodiment of a pin connector configured to connect to a chip for detecting a type of catheter and/or heating segment attached to the power source; and FIG. 14B is a side elevation view of one embodiment of a chip for detecting a type of catheter and/or heating segment attached to the power source.

DETAILED DESCRIPTION

The following detailed description describes the present embodiments with reference to the figures. In the figures, reference numbers label elements of the present embodiments. These reference numbers are reproduced below in connection with the discussion of the corresponding features.

Directional terms used herein, such as proximal, distal, upper, lower, clockwise, counterclockwise, etc., are used with reference to the configurations shown in the figures. For example, a component that is described as rotating clockwise when viewed from the perspectives shown in the figures may be said to rotate counterclockwise when viewed from the opposite perspective. Furthermore, the present embodiments may be modified by altering or reversing the positions or directions of movement of various components. Accordingly, directional terms used herein should not be interpreted as limiting.

Figure 1:
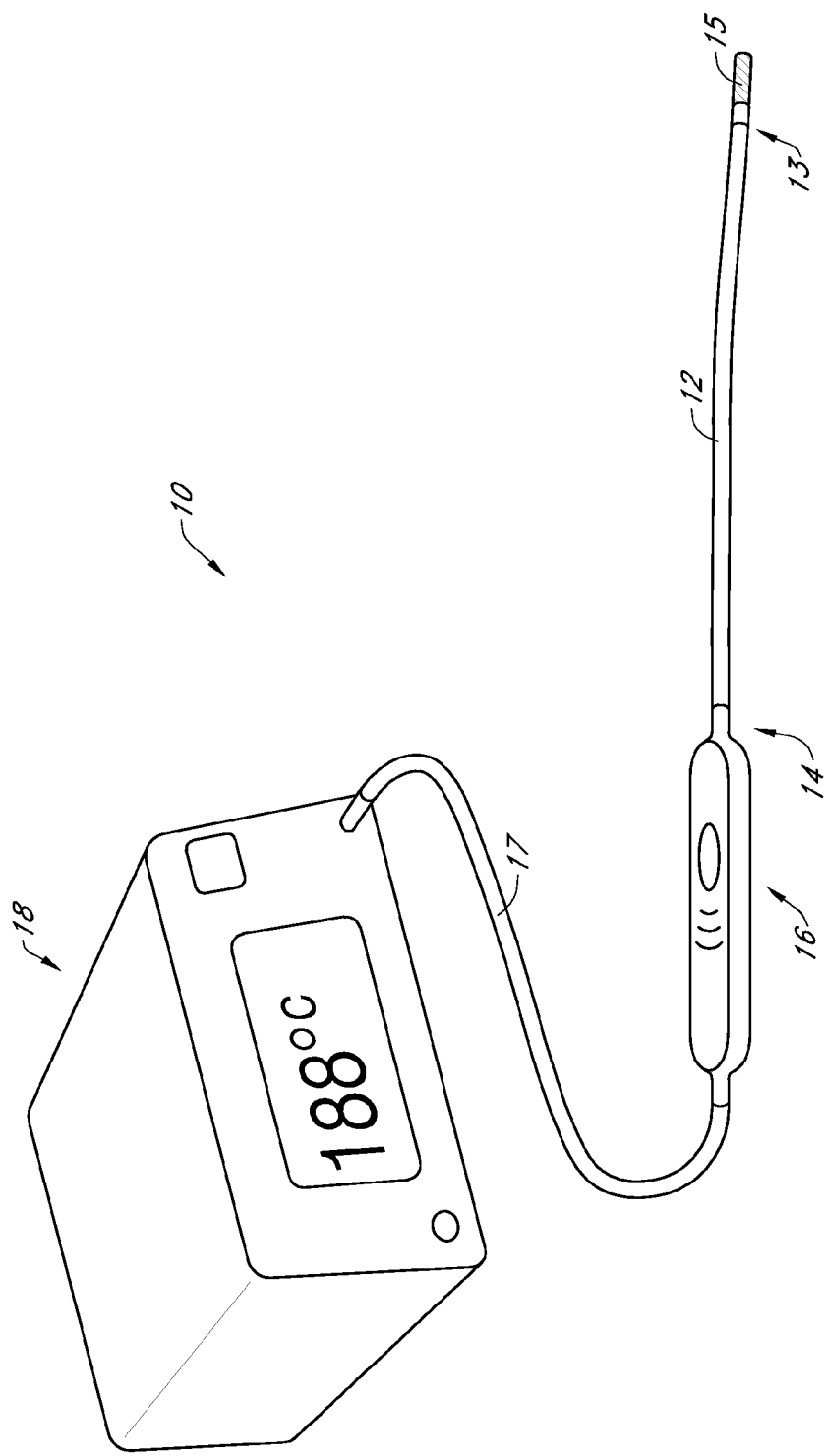
FIG. 1 is an overview of a medical treatment system having an adjustable length and/or diameter.

Referring to FIG. 1, a medical treatment system 10 may include a catheter shaft 12 having a distal end 13 and a proximal end 14. A heating segment 15 is operably attached adjacent the distal end 13 of the catheter shaft 12 and a handle 16 is attached at the proximal end 14 of the catheter shaft 12. A cable 17 electrically connects the heating segment 15 to a power source 18. The cable 17 may be integral to the handle 16 and removably connected to the power source 18. Alternatively, the cable 17 may be removably connected to the handle 16.

The heating segment 15 includes a heating element. The heating element may in some embodiments be a resistive coil, which may be driven, for example, by RF energy, ultrasound, or any other electrical form. Preferably, the relative resistance or impedance of the heating element is designed to correlate to, or match, the power source 18 to which the heating element is coupled. For example, the resistance of the heating element may be determined by a wire gage that relates to the catheter diameter, the energy required during treatment, and/or the power source specifications. The heating element may comprise a wide variety of conductive materials, such as, for example, nickel chromium (NICHROME®), Alloy 52, copper, stainless steel, titanium, zirconium, NITINOL®, ALUMEL®, KANTHANAL®, CHROMEL®, KOVAR®, combinations or alloys of the same and the like. The material for the heating element can be chosen to provide Resistance Temperature Detector (RTD) functionality, wherein temperature is indirectly measured as a function of impedance. Alloy 52 is considered to be one material suitable for providing RTD functionality to the resistive coil.

The heating segment 15 is secured at the distal end 13 of the elongate catheter shaft 12. The catheter shaft 12 may be used to maneuver the heating element into a desired placement within a HAS. In certain embodiments, the catheter shaft 12 comprises a biocompatible material having a low coefficient of friction. For example, the shaft may comprise polyether ether ketone (PEEK), polyethylene, or polytetrafluoroethylene (PTFE), such as TEFLON®. In other embodiments, the catheter shaft 12 may comprise polyimide, thermoplastic elastomer (TPE), such as HYTREL®, polyether block amide (PEBA), such as PEBAX®, nylon, or any other such suitable material.

In certain embodiments, the catheter shaft 12 is sized to fit within a vascular structure that may be between approximately 1 mm and approximately 25 mm in diameter and, preferably, between approximately 2 mm and approximately 18 mm. For instance, the catheter shaft 12 may have a maximum outer diameter of between approximately 4F (French) and approximately 8F and, more preferably, between approximately 6F and approximately 7F. In yet other embodiments, other sizes of catheters may be used. The proximal end 14 of the catheter shaft includes a handle 16 that may include a connection for interfacing with the power source 18 through the cable 17, and/or a port for fluid or guidewire passage.

In certain embodiments, the power source 18 comprises an alternating current (AC) source, such as an RF generator. In other embodiments, the power source 18 comprises a direct current (DC) power supply, such as, for example, a battery, a capacitor, or other power source 18 such as would be used for microwave heating. The power source 18 may also incorporate a controller that, through the use of a processor, applies power based at least upon readings from a temperature sensor or sensors (e.g., a thermocouple, a thermistor, a resistance temperature device, an optical or infrared sensor, combinations of the same or the like) located in or adjacent to the heating segment 15. For example, the controller may heat the tissue of a HAS or the heating segment 15 to a set temperature. In an alternative embodiment, the user selects a constant power output of the power source 18. For example, the user may manually adjust the power output relative to the temperature display from a temperature sensor in the heating segment 15.

Figure 1A:
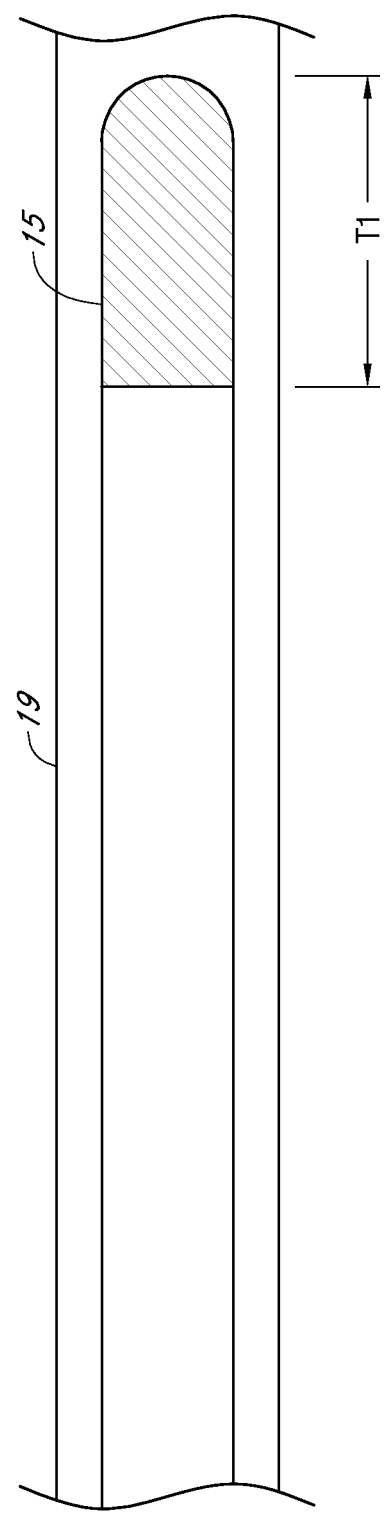
FIGS. 1A and 1B are side elevation views of an example procedure using the medical treatment system of FIG. 1.

The medical treatment system 10 may be used in various medical procedures, including endovenous treatments to treat venous reflux. Specifically, referring to FIG. 1A, a method may comprise inserting the heating segment 15 into a distalmost section of a HAS 19 to be treated. The heating segment 15 is then aligned with a first treatment location T1 within the HAS 19. In certain embodiments, a tumescent solution may be injected to surround and compress the HAS 19 (assisting in evacuation of fluid from within the HAS 19, providing a thermal heat sink to protect surrounding tissue, and providing anesthetic to the surrounding tissue). Compression of the HAS 19, such as through manual compression by the physician, may also be performed.

Figure 1B:
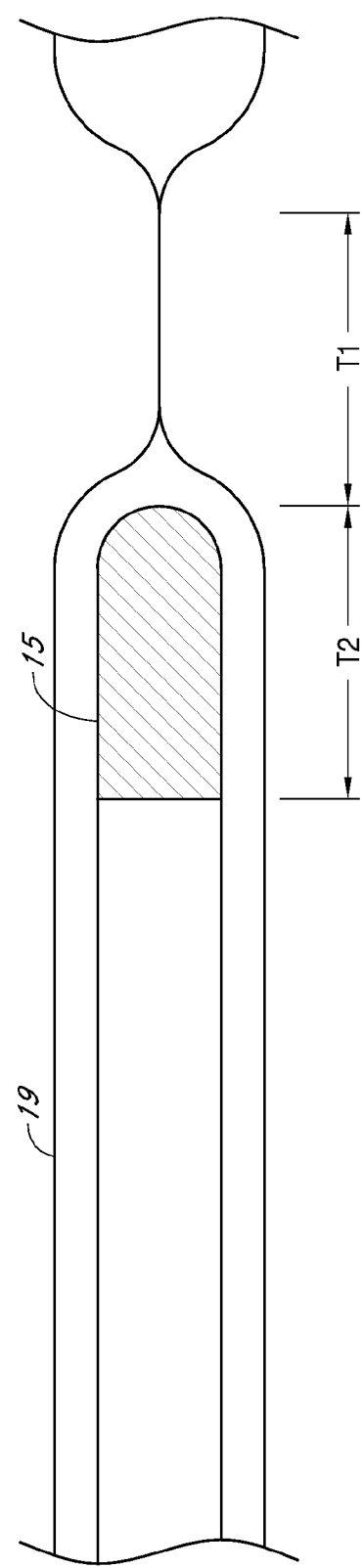

Power is then applied to the heating segment 15 for a desired length of time to treat the first treatment location T1. After a desired dwell time, such as after the HAS 19 has collapsed as shown in FIG. 1B, the power supply to the heating segment 15 may be reduced or shut off. With the power off (or substantially reduced), the heating segment 15 may then be moved proximally until the distal end of the heating segment 15 is adjacent to the proximal end of the first treatment location T1, as shown in FIG. 1B. At this second treatment location T2 within the HAS 19, power is again applied to the heating segment 15 for a desired length of time to treat the HAS 19 at the second treatment location T2. This process is repeated until the treatment of the HAS 19 is complete. In some embodiments, T1 and T2 may overlap. While T1 and T2 are shown adjacent to one another in the same HAS, T1 and T2 may be in different locations, such as different HAS. For example, as may be appreciated from the description below, T1 may be in the GSV, while T2 may be in a perforator vein flowing into the GSV, which may require devices of different length and/or diameter.

Adjustable Length Medical Treatment Devices

In clinical practice, such as for treating chronic venous insufficiency, the Great Saphenous Vein (GSV), the Small Saphenous Vein (SSV), and the Superficial Tributary Vein (STV) may all need to be treated in a single procedure. But, the lengths of these veins are different from one another. The example embodiment of FIGS. 2-5 is a medical treatment device having an adjustable treatment length, and is configured to solve the foregoing problem. In certain embodiments, the medical treatment device is a catheter configured for tissue ablation, but the inventive concepts of the present embodiments could be applied to other types of medical treatment devices.

Figure 2:
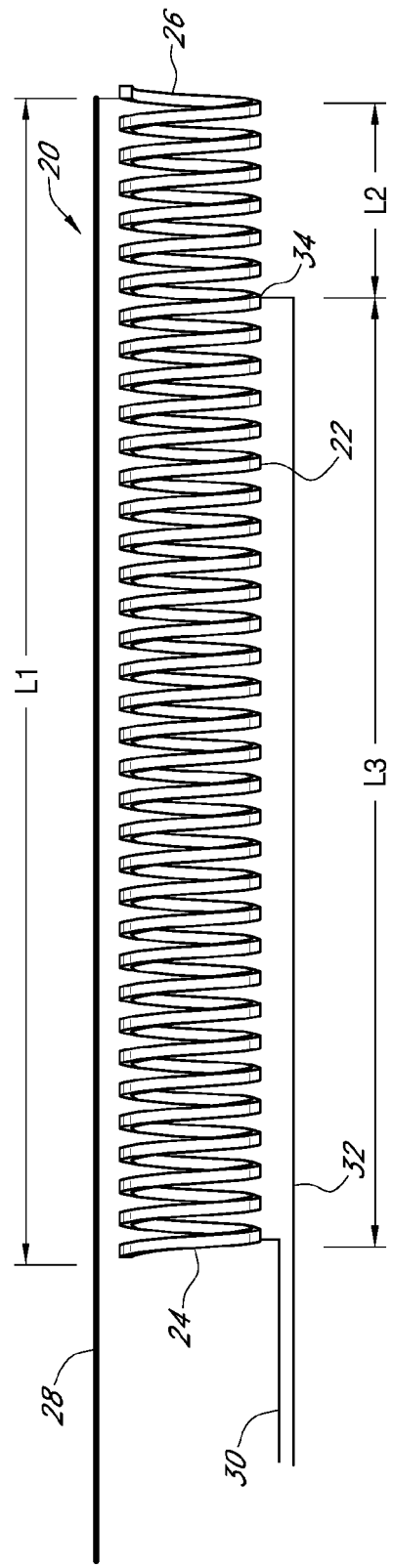
FIG. 2 is a side elevation view of one embodiment of a medical treatment device having an adjustable treatment length.

With reference to FIGS. 1 and 2, the heating segment 15 comprises a treatment device 20 including a heating element 22 having a proximal end 24 and a distal end 26. In the illustrated embodiment, the heating element 22 is an electrically resistive coil that heats up when electric current is delivered to it from the power source 18. However, in other embodiments the heating element 22 may comprise another type of device configured to heat tissue.

The illustrated treatment device 20 further includes a plurality of wires 28, 30, 32 extending between the power source 18 and the heating element 22, and electrically connected to the heating element 22. The wires 28, 30, 32 are configured to carry electrical current between the power source 18 and the heating element 22. The wires 28, 30, 32 are further configured to provide a plurality of electrical pathways extending between the power source and heating element 22, as explained in further detail below. In some embodiments, the wires 28, 30, 32 may be welded to the heating segment 22, such as by laser spot welding, resistance spot welding, etc. In other embodiments the wires 28, 30, 32 may be soldered to the heating element 22.

A first one of the wires 28 extends between the power source 18 and the distal end 26 of the heating element 22. A second one of the wires 30 extends between the power source and the proximal end 24 of the heating element 22. A third one of the wires 32 extends between the power source 18 and a point 34 along the heating element 22 intermediate the proximal and distal ends 24, 26 thereof. Current may be selectively applied to each of the wires 28, 30, 32 to create electrical pathways of different lengths, and thereby selectively change the effective length of the heating element 22.

For example, current may be applied through the first and second wires 28, 30 only (see FIG. 3), such that an electrical pathway extends between the power source 18, the proximal end 24 of the heating element 22, and the distal end 26 of the heating element 22, thereby defining a first treatment length L1 extending between the proximal and distal ends 24, 26 of the heating element 22. In another example, current may be applied through the first and third wire 28, 32 only (see FIG. 4), such that an electrical pathway extends between the power source 18, the distal end 26 of the heating element 22, and the intermediate point 34, thereby defining a second treatment length L2 extending between the intermediate point 34 and the distal end 26 of the heating element 22. In yet another example, current may be applied through the second and third wire 30, 32 only (see FIG. 5), such that an electrical pathway extends between the power source, the proximal end 24 of the heating element 22, and the intermediate point 34, thereby defining a third treatment length L3 extending between the intermediate point 34 and the proximal end 24 of the heating element 22.

With reference to FIG. 2, in certain embodiments the intermediate point 34, where the third wire 32 is electrically connected to the heating element 22, may be offset from a lengthwise center of the heating element 22. In such embodiments, three different treatment lengths may be achieved, because a distance L3 between the proximal end 24 and the intermediate point 34 is different from a distance L2 between the distal end 26 and the intermediate point 34 (with the entire length L1 of the heating element 22 providing the third treatment length). In other embodiments, however, the intermediate point 34 may be at the lengthwise center of the heating element 22, such that L2 and L3 are the same length.

Figure 3:
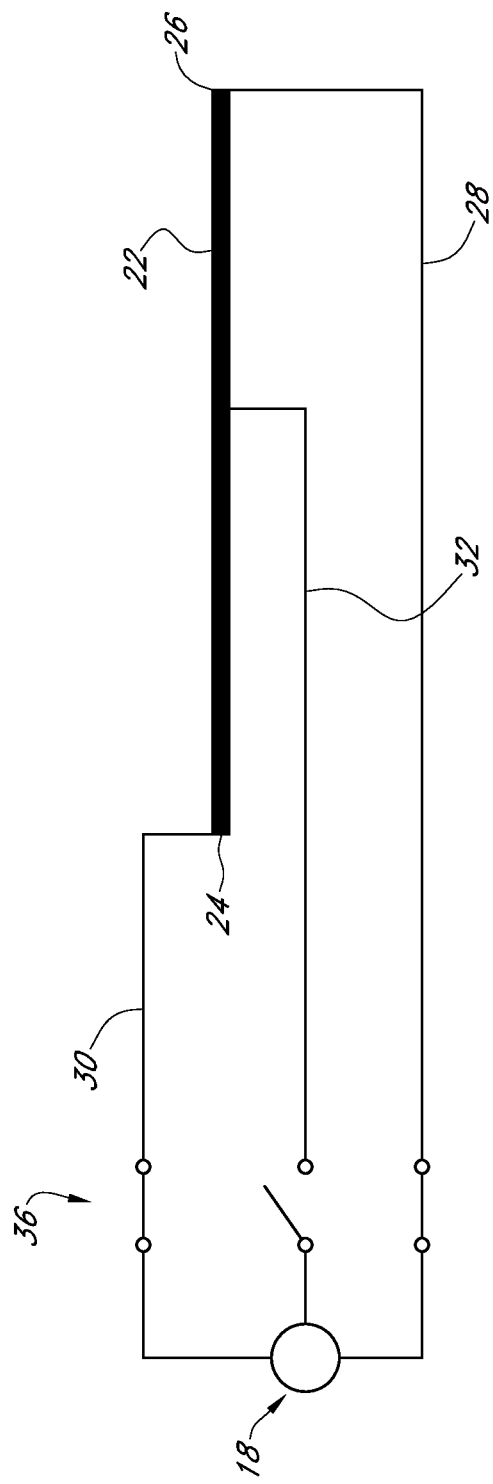
FIG. 3 is a schematic diagram of a first configuration for power delivery to the medical treatment device of FIG. 2.
Figure 4:
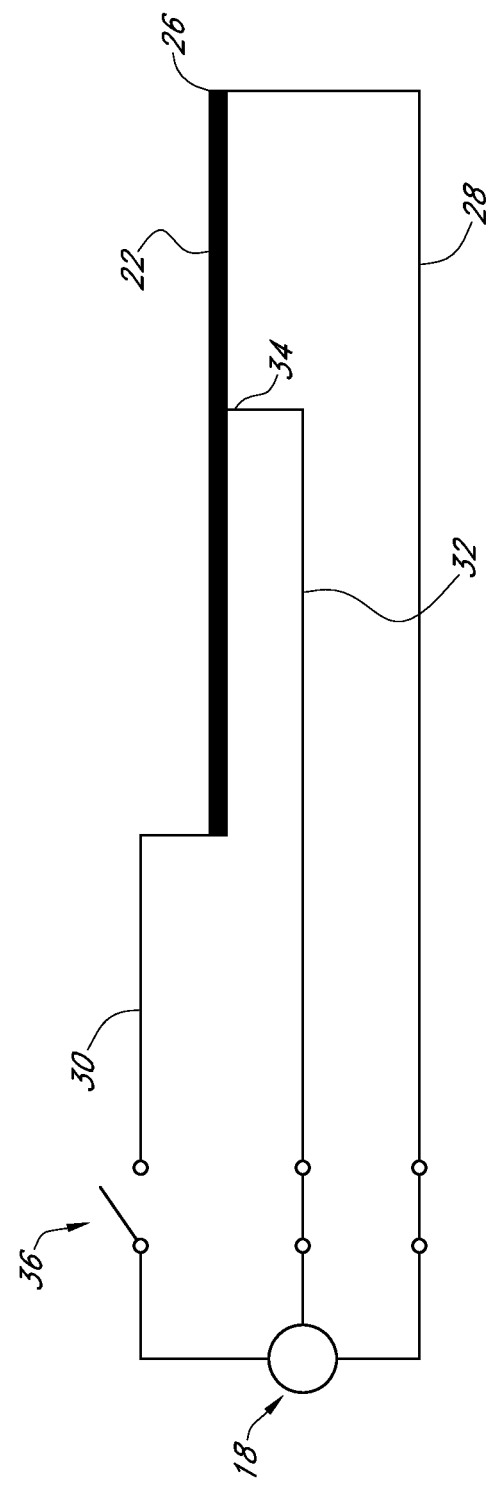
FIG. 4 is a schematic diagram of a second configuration for power delivery to the medical treatment device of FIG. 2.
Figure 5:
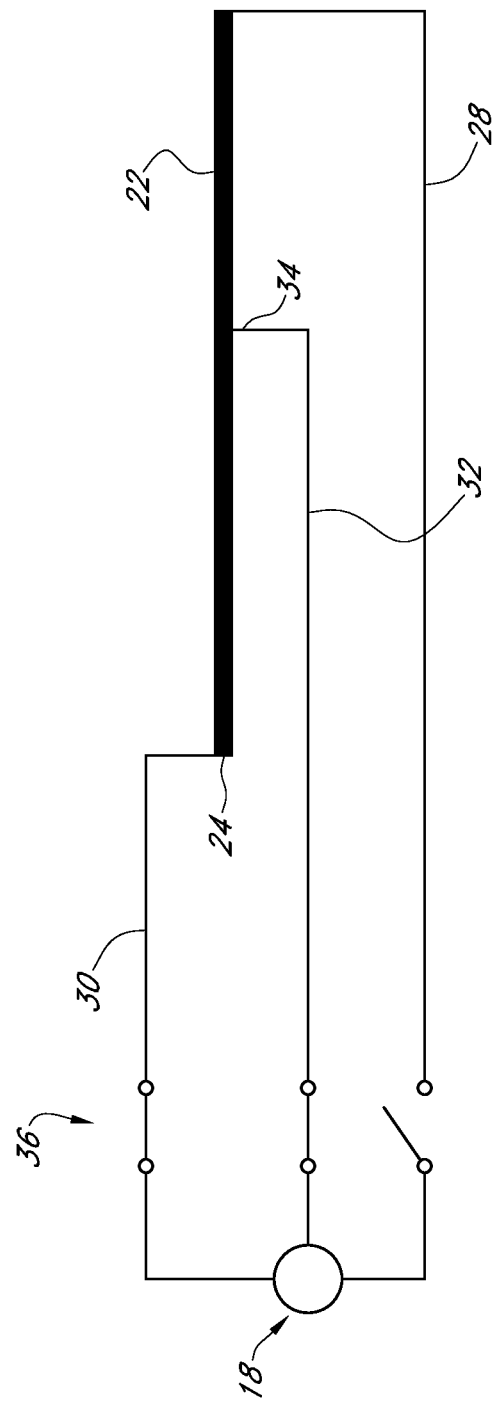
FIG. 5 is a schematic diagram of a third configuration for power delivery to the medical treatment device of FIG. 2.

The present embodiments may include one or more switching mechanisms 36 (FIGS. 3-5) to select which of the treatment lengths is active at any given moment. The switching mechanism 36 may be on the handle 16, or may be part of the power source 18, such as part of a controller or as individual switches. For example, FIGS. 3-5 schematically illustrate the three electrical pathways described above. With reference to FIG. 3, the switching mechanism 36 closes the circuit between the power source 18 and the first and second wires 28, 30, thereby creating an electrical pathway between the power source 18, the proximal end 24 of the heating element 22, and the distal end 26 of the heating element 22. With reference to FIG. 4, the switching mechanism 36 closes the circuit between the power source 18 and the first and third wires 28, 32, thereby creating an electrical pathway between the power source 18, the intermediate point 34 of the heating element 22, and the distal end 26 of the heating element 22. With reference to FIG. 5, the switching mechanism 36 closes the circuit between the power source 18 and the second and third wires 30, 32, thereby creating an electrical pathway between the power source 18, the intermediate point 34 of the heating element 22, and the proximal end 24 of the heating element 22.

In certain embodiments, the power source 18 may be configured to automatically distinguish between the various treatment lengths L1, L2, L3 and adjust a level of power delivery for a desired energy output. For example, in certain embodiments an impedance value of the heating element 22 may be measured to determine the treatment length. Alternatively, if the heating element 22 is a coil, it will generate a magnetic field when it is energized. The length of the heating element 22 can then be determined by measuring the strength of the magnetic field. In another alternative, a switch may be provided on the handle 16 to indicate the treatment length. In yet another alternative, power delivery to the heating element 22 can be adjusted automatically to adapt different treatment lengths based on temperature feedback from temperature sensors located in the heating element 22.

In certain embodiments, the maximum power output to the heating element 22 is 65 W, and the target temperature of the heating element 22 is 120° C. For example, in various methods the temperature of the heating element 22 may increase from ambient temperature to 120° C. in 5 seconds, and be maintained at 120° C. for another 15 seconds. The system may adjust the power output automatically according to a temperature feedback loop, such as with a temperature sensor located in or near the heating element 22. Normally, during the temperature ramp up period (the first 5 s), a greater amount of power is supplied to the heating element as compared to the temperature maintenance period (the last 15 s).

The embodiments of FIGS. 2-5 may be used in a variety of methods, including treatment procedures such as tissue ablation to treat venous reflux, as described above (FIGS. 1A-1B). For example, one such method may comprise positioning the heating element 22 of the device of FIG. 2 adjacent a first treatment location T1 in a hollow anatomical structure. Power may then be delivered during a first power delivery phase from a power source 18 connected to the heating element 22 along the first electrical pathway extending between the power source 18, the proximal end 24 of the heating element 22, and the distal end 26 of the heating element 22, thereby defining a first treatment length L1 between the proximal and distal ends 24, 26 of the heating element 22. Power may then be delivered during a second power delivery phase from the power source 18 along the second electrical pathway extending between the power source 18, the distal end 26 of the heating element 22, and the intermediate point 34 on the heating element 22, thereby defining the second treatment length L2 between the distal end 26 of the heating element 22 and the intermediate point 34. The foregoing method may further comprise, between the first and second power delivery phases, positioning the heating element 22 adjacent to a second treatment location T2 in the HAS, and switching power delivery from the first electrical pathway to the second electrical pathway. In one example, the heating element 22 may be positioned in a perforator vein connecting the target HAS and the deep venous system. Typically, the perforator vein is shorter than the target HAS, and thus might require a shorter length of the heating element 22 to be used. The heating element 22 may then be pulled back into the target HAS and the procedure continued within the target HAS using a longer length of the heating element 22. In an alternative embodiment, the second power delivery phase may comprise delivering power from the power source along the third electrical pathway extending between the power source 18, the proximal end 24 of the heating element 22, and the intermediate point 34 on the heating element 22, thereby defining the third treatment length L3 between the proximal end 24 of the heating element 22 and the intermediate point 34. Other embodiments may comprise methods of varying a treatment length of a tissue ablation catheter.

Adjustable Length and/or Diameter Medical Treatment Devices

The embodiment of FIGS. 6-10 is another example embodiment of a heating segment 15 having an adjustable treatment length, as well as an adjustable treatment diameter, comprising a shaft connector 40 and various heating assemblies 58, 60, 62. As in the embodiment of FIGS. 2-5, the present device includes an elongate catheter shaft 12, the features and configuration of which may be similar to that described above. Also as in the embodiment of FIGS. 2-5, the present device is connectable to a power source 18, the features and configuration of which may be similar to that described above.

Figure 6:
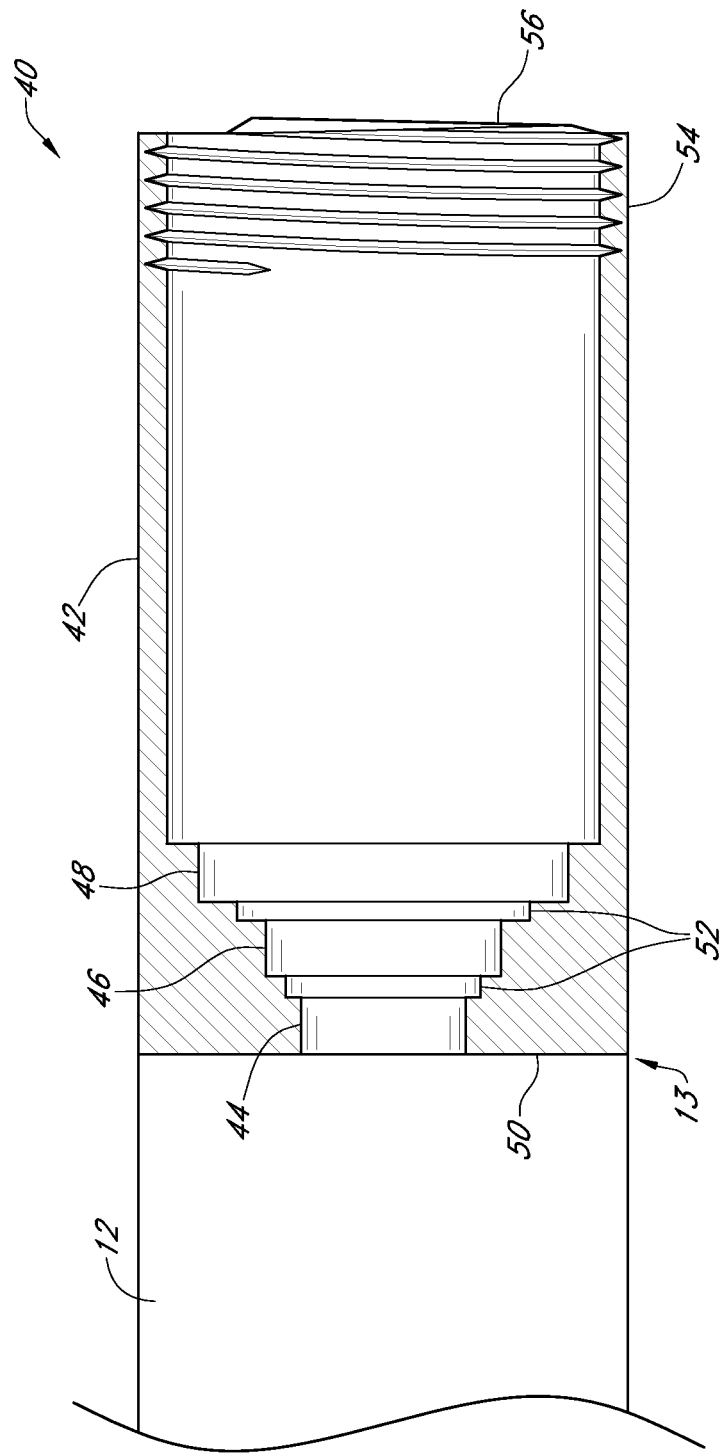
FIG. 6 is a side elevation view of one embodiment of a portion of a medical treatment device having an adjustable treatment length.

With reference to FIG. 6, the shaft connector 40 is secured adjacent the distal end 13 of the catheter shaft 12. In the illustrated embodiment, the shaft connector 40 comprises a substantially cylindrical body 42 having a plurality of shaft electrical contacts 44, 46, 48 near a proximal end 50 of the shaft connector 40. The shaft electrical contacts 44, 46, 48 have a stepped configuration in which the contacts are spaced in the axial direction and also in the radial direction. In the illustrated embodiment, three shaft electrical contacts 44, 46,

48 are shown, but in alternative embodiments any number of shaft electrical contacts 44, 46, 48 may be provided.

As illustrated, the shaft electrical contacts 44, 46, 48 comprise a plurality of rings, each having a progressively greater diameter in the proximal-to-distal direction, and each being axially spaced. A proximal-most ring comprises a first shaft electrical contact 44, a central ring comprises a second shaft electrical contact 46, and a distal-most ring comprises a third shaft electrical contact 48. Insulating rings 52 are interposed between adjacent shaft electrical contacts 44, 46, 48. The stepped proximal end 50 of the shaft connector 40 is configured to mate with a coupler at a proximal end of each of a plurality of heating assemblies, as described further below.

The shaft connector 40 further comprises a shaft mechanical coupler 54 at a distal end 56 of the shaft connector 40. The illustrated embodiment of the shaft mechanical coupler 54 comprises a plurality of internal screw threads, but in alternative embodiments may comprise other structures, such as latches. The shaft mechanical coupler 54 is configured to mate with a coupler at a proximal end of each of the plurality of heating assemblies.

The shaft connector 40, including the electrical contacts 44, 46, 48, the insulators 52, and the cylindrical body 42, may comprise any suitable materials. For example, the cylindrical body 42 may be a polymer, which may be plated with a metal, such as stainless steel. The electrical contacts 44, 46, 48 may be metallic, such as iron, gold, copper, etc. The insulators 52 may be rubber or plastic, for example.

Figure 7:
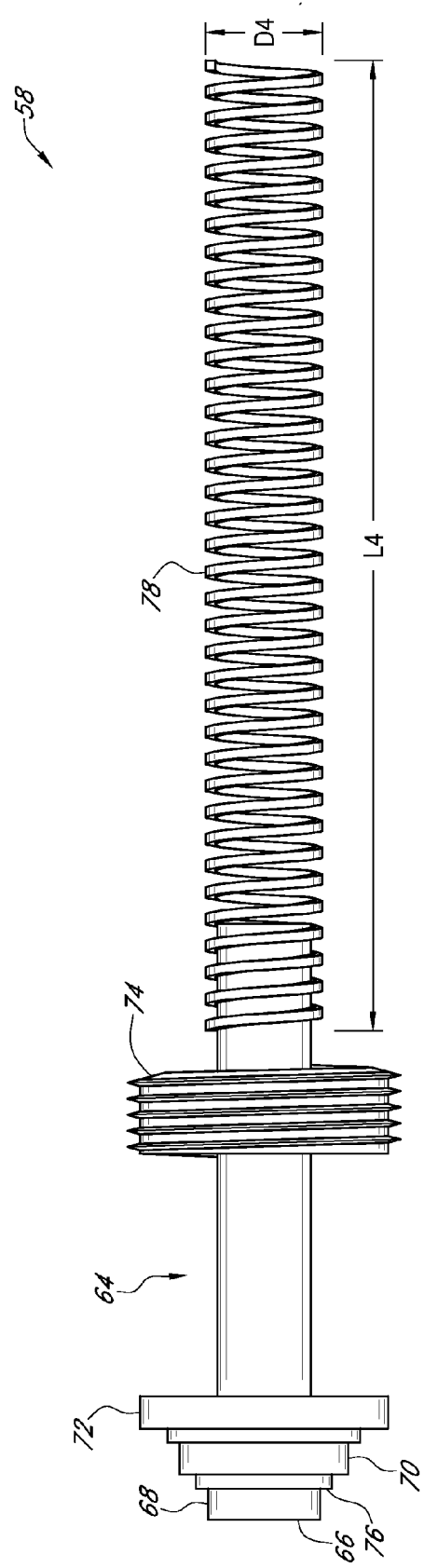
FIG. 7 is a side elevation view of one embodiment of another portion of the medical treatment device of FIG. 6 having an adjustable treatment length.
Figure 8:
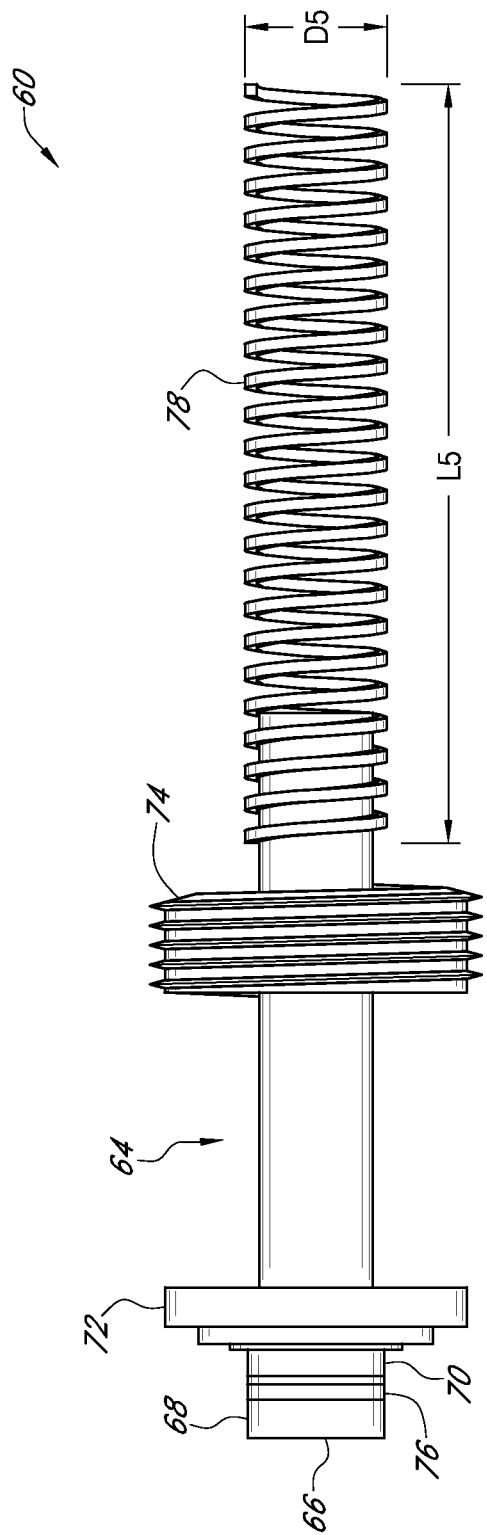
FIG. 8 is a side elevation view of one embodiment of another portion of the medical treatment device of FIG. 6 having an adjustable treatment length.
Figure 9:
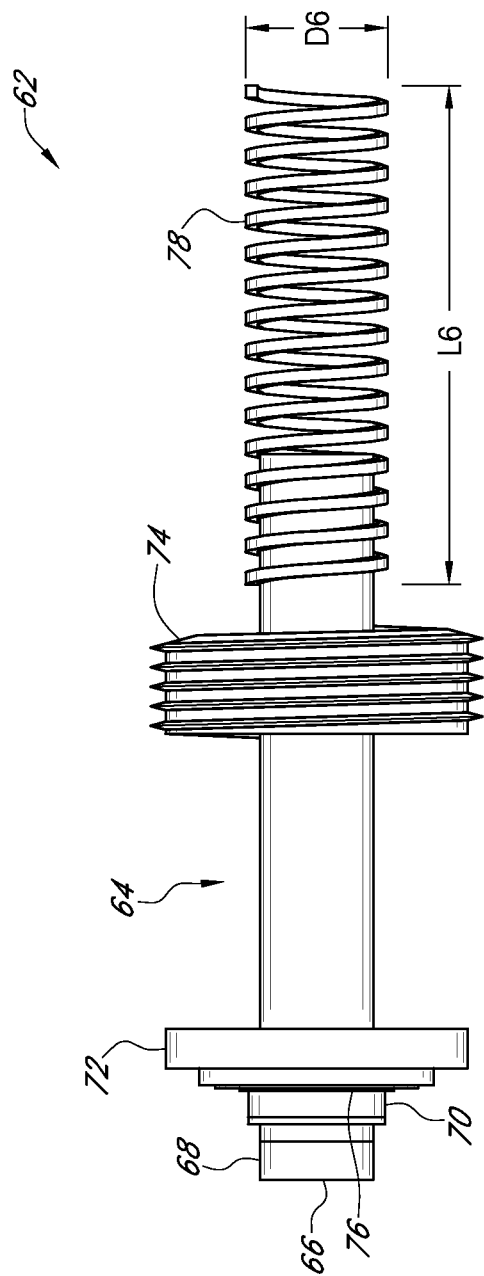
FIG. 9 is a side elevation view of one embodiment of another portion of the medical treatment device of FIG. 6 having an adjustable treatment length.

With reference to FIGS. 7-9, the present heating segment 15 further comprises a plurality of heating assemblies 58, 60, 62, each having a different length and/or diameter. In the illustrated embodiment, three heating assemblies 58, 60, 62 are shown, but in alternative embodiments any number of heating assemblies 58, 60, 62 may be provided with the catheter 12. Each of the heating assemblies 58, 60, 62 has a heating element connector 64 adjacent a proximal end 66 thereof, with each of the heating element connectors 64 having a plurality of heating element electrical contacts 68, 70, 72. Each of the heating assemblies 58, 60, 62 further includes a heating assembly mechanical coupler 74 adjacent the proximal end 66, but distal of the heating element electrical contacts 68, 70, 72. The heating element connectors 64 are connectable to the shaft connector 40 to selectively couple the heating assemblies 58, 60, 62 to the catheter shaft 12, as described further below.

The heating element electrical contacts 68, 70, 72 have a stepped configuration in which the contacts are spaced in the axial direction and also in the radial direction, and are configured to be complementary to the shaft electrical contacts 44, 46, 48. In the illustrated embodiment, three heating element electrical contacts 68, 70, 72 are shown for each of the heating assemblies 58, 60, 62, but in alternative embodiments any number of heating element electrical contacts may be provided. Also in the illustrated embodiment, the heating element mechanical coupler 74 comprises a plurality of external screw threads that mate with the shaft mechanical coupler 54 to releasably couple the heating assemblies 58, 60, 62, to the shaft connector 40. Alternative embodiments may comprise other structures to mate with the shaft mechanical coupler 54, such as latches.

With further reference to FIGS. 7-9, the proximal end 66 of each of the heating assemblies 58, 60, 62 includes a proximal-most or first electrical contact 68, a distal-most or third electrical contact 72, and an intermediate or second electrical contact 70. Insulating rings 76 are interposed between adjacent heating element electrical contacts 68, 70, 72. The diameters of the heating element electrical contacts 68, 70, 72 vary from one embodiment to another, such that the heating element electrical contacts 68, 70, 72 achieve electrical connection with the shaft electrical contacts 44, 46, 48 in various combinations.

For example, with the shaft connector 40 releasably engaged with the proximal end 66 of the heating assemblies 58, 60, 62, the heating element electrical contacts 68, 70, 72 are configured to selectively contact various combinations of the shaft electrical contacts 44, 46, 48 in order to modulate the power delivery to the heating assemblies 58, 60, 62 based upon the length of the heating assemblies 58, 60, 62.

Distally of the heating element mechanical coupler 74, each heating assembly 58, 60, 62 further comprises a heating element 78. In the illustrated embodiment, the heating element 78 is an electrically resistive element, such as an electrically restrictive coil, but in other embodiments may comprise other structures, such as one or more radio frequency (RF) electrodes. In FIGS. 7-9, each of the heating elements 78 is illustrated with a different length, with the embodiment of FIG. 7 having the greatest length L4, the embodiment of FIG. 9 having the shortest length L6, and the embodiment of FIG. 8 having a length L5 intermediate of FIGS. 7 and 9. Each heating assembly 58, 60, 62 also has a diameter D4, D5, D6, respectively, which may also be different. In certain embodiments, only the length L4, L5, L6 of the heating elements 78 vary. In other embodiments, only the diameters D4, D5, D6 of the heating elements 78 vary. In still other embodiments, both the length L4, L5, L6 and the diameters D4, D5, D6 of the heating elements 78 vary. Each of the heating assemblies 58, 60, 62 further has a different configuration at the stepped proximal end 66, such that the heating element electrical contacts 68, 70, 72 will contact the shaft electrical contacts 44, 46, 48 in different ways as each heating element 78 is sequentially connected to the shaft connector 40, as described below.

With reference to FIG. 7, the first, second, and third heating element electrical contacts 68, 70, 72 are sized and configured to be matingly received within the corresponding first, second and third shaft electrical contacts 44, 46, 48 such that electrical contact is achieved between all electrical contacts on each component. When so connected, the power source 18 detects that all of the shaft electrical contacts 44, 46, 48 are in electrical connection with all of the heating element electrical contacts 68, 70, 72, and adjusts the power output accordingly to deliver a desired level of treatment power based on the length L4 of the heating element 78.

With reference to FIG. 8, the first and third heating element electrical contacts 68, 72 are sized and configured to be matingly received within the corresponding shaft electrical contacts 44, 48 such that electrical contact is achieved between only the first and third electrical contacts on each component (the second electrical contacts on each component are not connected). When so connected, the power supply detects that only the first and third shaft electrical contacts 44, 48 are in electrical connection with only the first and third heating element electrical contacts 68, 72, and adjusts the power output accordingly to deliver a desired level of treatment power based on the length L5 of the hearing element 78.

With reference to FIG. 9, the second and third heating element electrical contacts, 70, 72 are sized and configured to be matingly received within the corresponding second and third shaft electrical contacts 46, 48 such that electrical contact is achieved between only the second and third electrical contacts on each component (the first electrical contacts on each component are not connected). When so connected, the power supply detects that only the second and third shaft electrical contacts 46, 48 are in electrical connection with only the second and third heating element electrical contacts 70, 72, and adjusts the power output accordingly to deliver a desired level of treatment power based on the length L6 of the heating element 78.

With respect to the embodiment of FIGS. 6-9, certain embodiments may comprise an indicator adjacent a proximal end of the catheter shaft 12 that indicates which of the heating assemblies 58, 60, 62 is connected to the shaft. As discussed above, the power source 18 automatically detects which of the heating assemblies 58, 60, 62 is connected at any given time and adjusts the power output accordingly. Upon determining which of the heating assemblies 58, 60, 62 is connected, the power source 18 may also set a visual appearance of the indicator accordingly. For example, the indicator may comprise one or more light-emitting diodes (LEDs) 82, (see FIG. 10), such as a plurality of monochromatic or polychromatic LEDs. In one embodiment comprising three heating assemblies 58, 60, 62, the indicator may comprise three LEDs of the same color, and a single one of the LEDs may be illuminated when the shortest heating element 78 is connected, three of the LEDs may be illuminated when the longest heating element 78 is connected, and two of the LEDs may be illuminated when the intermediate length heating element 78 is connected.

Figure 10:
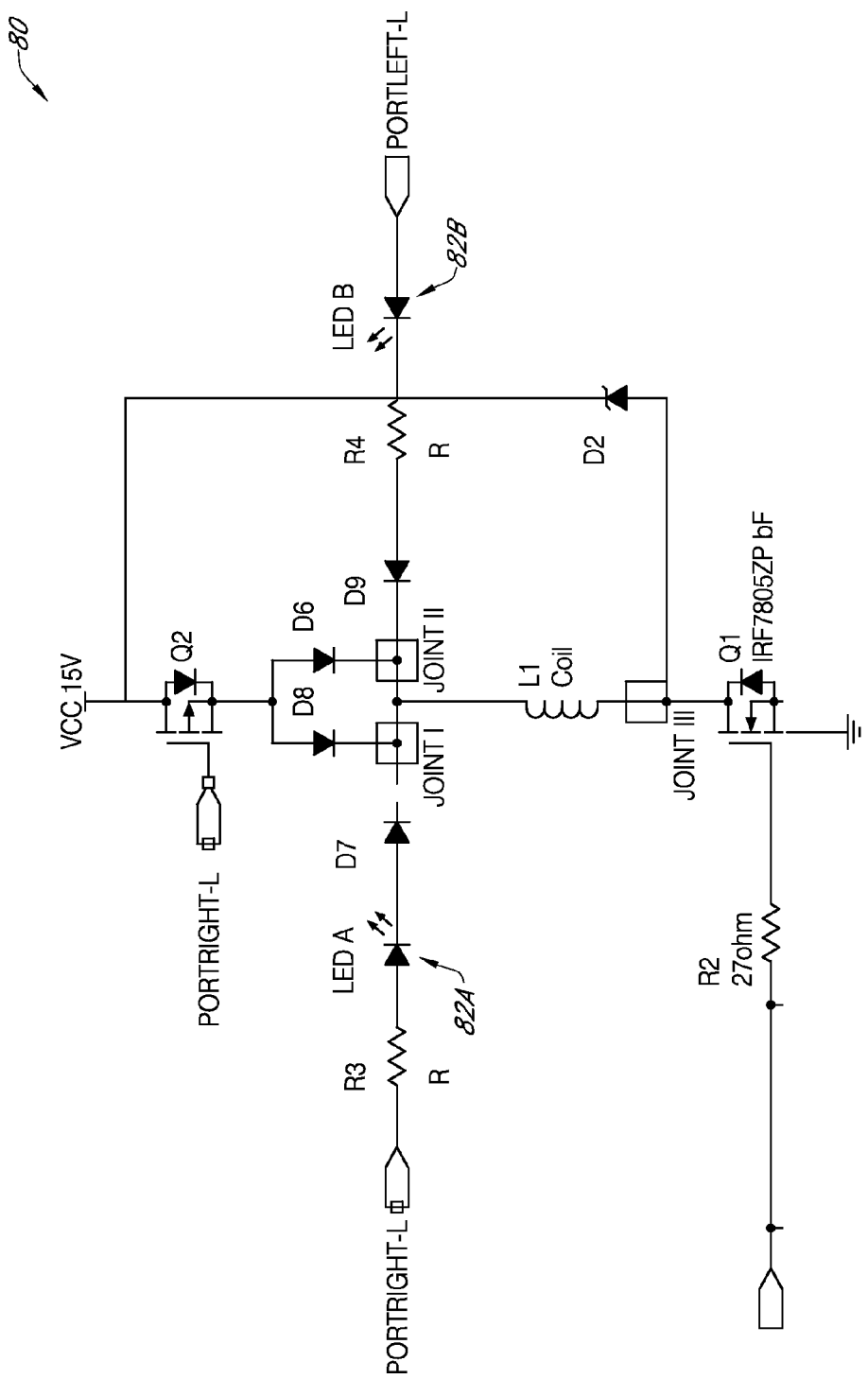
FIG. 10 is a circuit diagram of one embodiment of an electrical circuit configured for use in the medical treatment device of FIGS. 6-9.

FIG. 10 is a circuit diagram 80 showing one example of an alternative embodiment having two LEDs 82A, 82B, and specifically how the three electrical contacts on both the shaft connector 40 and the heating assemblies 58, 60, 62 can trigger three connection conditions to control which of the two LEDs 82A, 82B is illuminated. In FIG. 10, RF power is generated using power from power supply VCC_15V. Power for LED 82A is provided by a PORTRIGHT-L connection and power for LED 82B is provided by a PORTLEFT-L connection. JOINTS I, II, and III correspond to connections provided by the electrical connectors discussed with respect to FIGS. 6-9. As an example, when connecting junction points JOINT I and JOINT III, electrical power from PORTRIGHT-L passes through R3, LED A 82A, D7, L1, and Q1 to ground. LED A 82A is thus illuminated to indicate that the heating assembly 60 of FIG. 8 is connected. When connecting junction points JOINT II and JOINT III, electrical power from PORTLEFT-L passes through R4, LED B 82B, D9, L1, and Q1 to ground. LED B 82B is thus illuminated to indicate that the heating assembly 62 of FIG. 9 is connected. When connecting junction points JOINT I, JOINT II, and JOINT III, both the LED A 82A and LED B 82B circuits are activated and both LED A 82A and LED B 82B are illuminated to indicate that the heating assembly 58 of FIG. 7 is connected. RF energy is activated from VCC_15V via Q2, D6, and/or D8, L1, and Q1 to ground, to achieve RF energy delivery to the coil. During actual RF energy delivery, LED A 82A and/or LED B 82B will be off, since the RF voltage is higher than the LED driving voltage at JOINT I and/or JOINT II.

The embodiment of FIGS. 6-9 may be used in a variety of methods, including treatment procedures such as tissue ablation to treat venous reflux, as described above with reference to FIG. 1A. For example, one such method may comprise connecting a first heating assembly 58 having a heating element with a first length L4 to a distal end of an elongate catheter shaft 12, and ablating tissue with the first heating element 78 at a first treatment location T1. The first heating assembly 58 may then be disconnected from the catheter shaft 12, and a second heating assembly 60 having a heating element 78 with a second length L5 may be connected to the distal end of the catheter shaft 12. The first and second lengths L4, L5 may be different. The method may further comprise ablating tissue with the second heating element 60 at a second treatment location T2. When the first heating assembly 58 is connected to the catheter shaft, heating element electrical contacts 68, 70, 72 on the first heating assembly 58 may contact a first combination of shaft electrical contacts 44, 46, 48 on the shaft. When the second heating assembly 60 is connected to the catheter shaft 12, heating element electrical contacts 68, 70, 72 on the second heating assembly 60 may contact a second combination of the shaft electrical contacts 44, 46, 48. When any of the heating assemblies 58, 60, 62 is connected to the catheter shaft 15, a power source 18 coupled to the device may automatically detect a length of the connected heating element 78 based on which of the shaft electrical contacts 44, 46, 48 is in contact with the heating element electrical contacts 68, 70, 72. In response, the power supply 18 may adjust a level of power delivery for a desired energy output.

Adjustable Diameter Medical Treatment Devices

Figure 11:
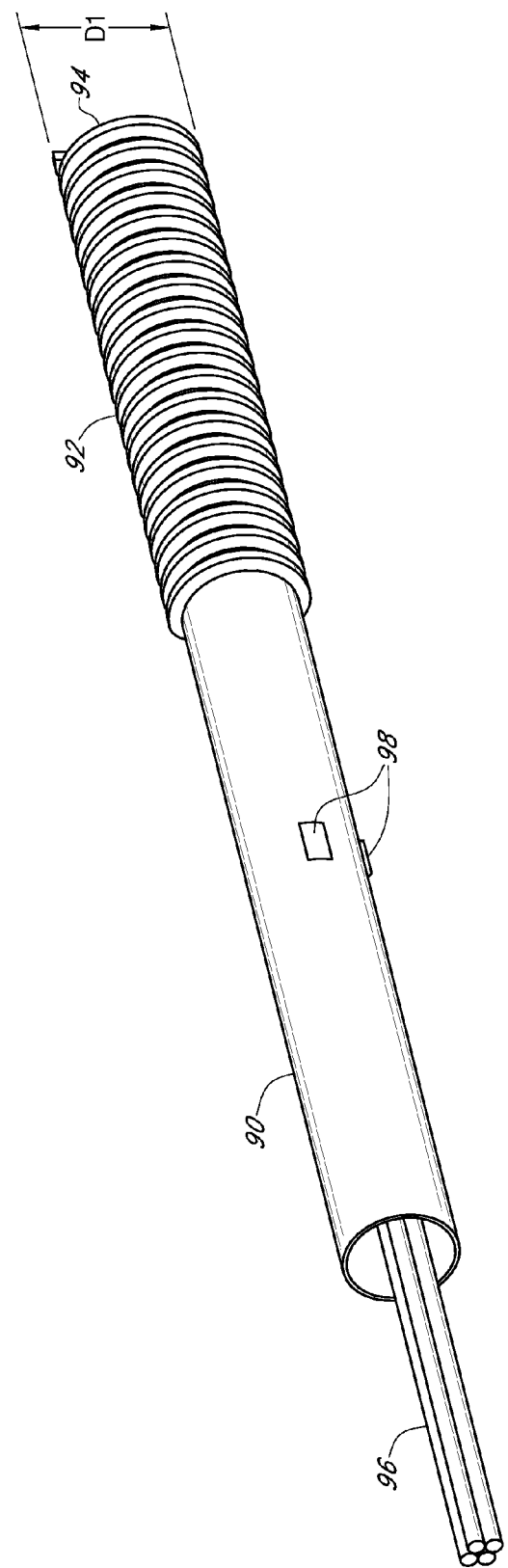
FIG. 11 is a side perspective view of one embodiment of a portion of a medical treatment device having an adjustable treatment diameter.
Figure 12:
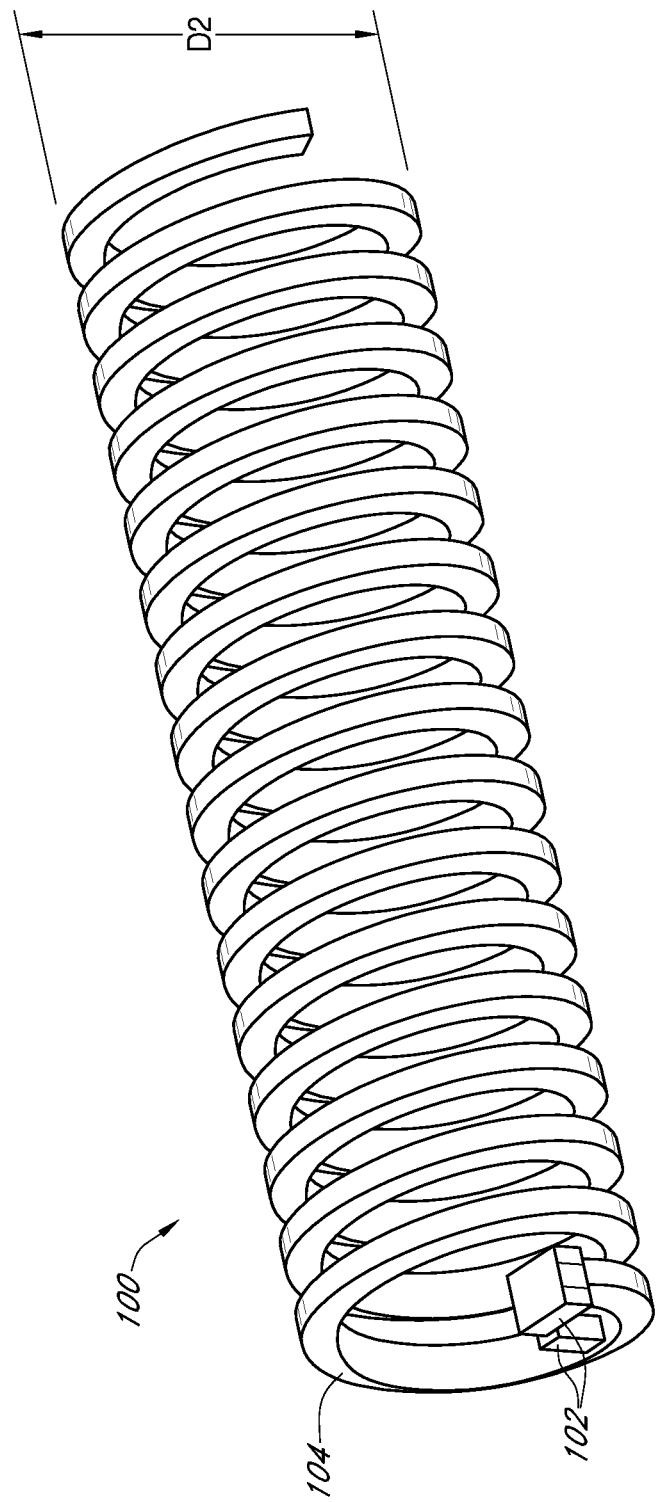
FIG. 12 is a side perspective view of one embodiment of another portion of the medical treatment device of FIG. 11 having an adjustable treatment diameter.
Figure 13:
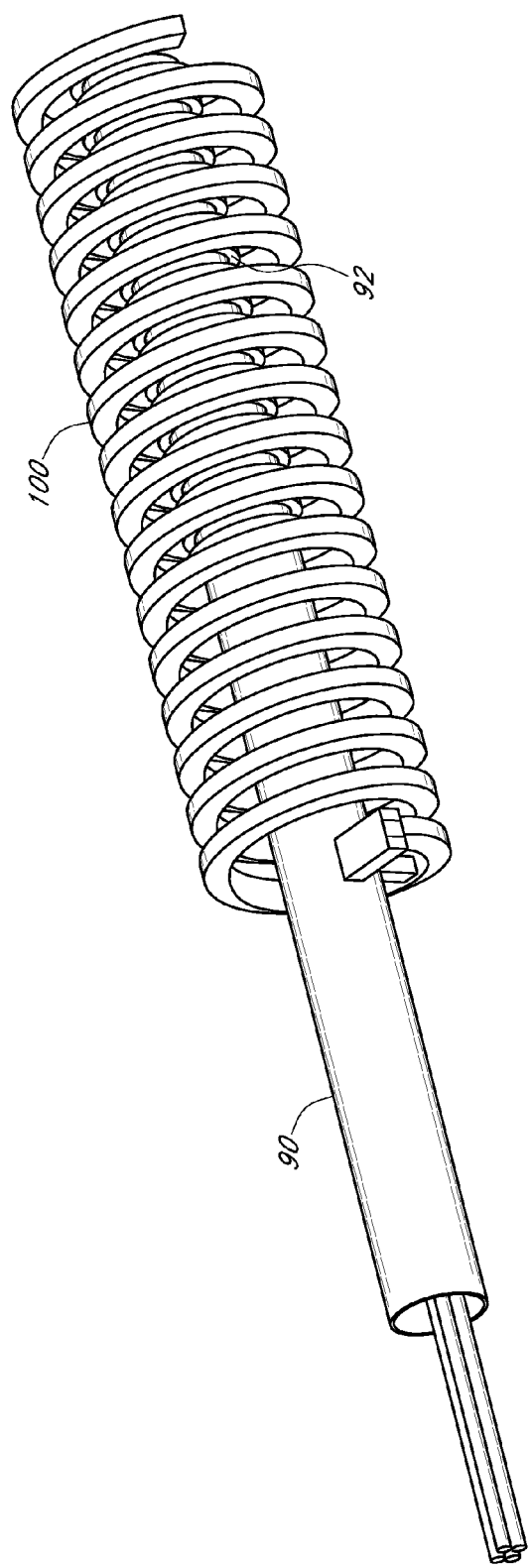
FIG. 13 is a side perspective view of the portions of FIGS. 11 and 12 together.

As described above, the Great Saphenous Vein (GSV), the Small Saphenous Vein (SSV), and the Superficial Tributary Vein (STV) may all need to be treated in a single procedure. But, the diameters of these veins are different from one another. The example embodiment of FIGS. 11-13 is a medical treatment device having an adjustable treatment diameter, and is configured to solve the foregoing problem. In certain embodiments, the medical treatment device is a catheter configured for tissue ablation as described above, but the inventive concepts of the present embodiments could be applied to other types of medical treatment devices.

FIGS. 11-13 illustrate one example embodiment of a medical treatment device having an adjustable treatment diameter. With reference to FIG. 11, the device includes a flexible, tubular catheter shaft 90 having a nominal diameter heating element 92 at a distal end 94. In the illustrated embodiment, the nominal diameter heating element 92 is a resistive heating coil that encircles the catheter 90. However, in other embodiments the nominal diameter heating element 92 may comprise another type of treatment device, such as one or more electrodes. The nominal diameter heating element 92 has an outer diameter, referred to herein as a nominal diameter D1, that may be for example 5F. Electrically conductive wires 96 extend through the catheter shaft 90 in order to connect the nominal diameter heating element 92 to a power source 18. A temperature sensor (not shown), such as a thermocouple, may also be provided so that temperature at a treatment site may be monitored.

With further reference to FIG. 11, an outer surface of the catheter shaft 90 includes a pair of electrical contacts 98 located proximally of the nominal diameter heating element 92. In the illustrated embodiment, the contacts 98 are spaced radially by 90°, but in alternative embodiments could be configured differently such as different radial spacing or axial spacing. The electrical contacts 98 provide connection points for a larger diameter heating element 100, which is illustrated in FIG. 12 and which can be attached to the catheter 90 when needed. The electrical contacts 98 are also connected to the power source 18 through the wires 96, so that the power source can deliver power to the larger diameter heating element 100.

With further reference to FIG. 12, the larger diameter heating element 100 has a diameter D2 larger than that of the nominal diameter heating element 92. For example, the diameter of the larger diameter heating element 100 may be 7F. The larger diameter heating element 100 is thus adapted to treat larger hollow anatomical structures. The larger diameter heating element 100 includes a pair of electrical contacts 102 at its proximal end 104 that are positioned to achieve removable electrical connection with the electrical contacts 98 on the catheter shaft 90 when the larger diameter heating element 100 is positioned around the distal end 94 of the catheter 90 over the nominal diameter heating element 92, as shown in FIG. 13. While not shown, a mechanical coupling may be provided to secure the larger diameter heating segment 100 to the catheter 90, such as a screw joint, a latch joint, a magnetic clip, or any other mechanical or electromechanical method. In addition to being of a larger diameter, larger diameter heating element 100 may also have a longer length, as shown.

In certain embodiments, the power source 18 may be configured to automatically detect whether the larger diameter heating element 100 is connected to the distal end 94 of the catheter shaft 90, and to adjust an energy output to the larger diameter heating element 100 to a desired energy output. For example, detecting whether the larger diameter heating element 100 is connected may comprise measuring at least one of a resistance value and an inductance value of the larger diameter heating element 100 by passing a detecting current through the larger diameter heating element 100. In an alternative embodiment, detecting whether the larger diameter heating element 100 is connected may comprise detecting whether a detecting current is flowing between the electrical contacts 98 on the catheter 90.

While the illustrated embodiment shows only one larger diameter heating element 100, the present embodiments may include any number of larger diameter heating elements of various diameters. Each such element may be connectable to the catheter shaft 90 sequentially to further enhance the adaptability of the treatment device to various different applications at different locations in the body, or to accommodate unexpected larger vasculature of a patient without the need to open another complete device having a different diameter during the procedure.

The embodiment of FIGS. 11-13 may be used in a variety of methods, including treatment procedures such as tissue ablation to treat venous reflux, as described above with reference to FIGS. 1A and 1B. For example, one such method may comprise positioning a nominal diameter heating element 92 adjacent to a first treatment location T1, wherein the first heating element 92 is disposed at a distal end 94 of an elongate catheter shaft 90, and the nominal diameter heating element 92 has a first outer diameter D1. The target tissue may then be ablated with the nominal diameter heating element 92. A larger diameter heating element 100 may then be connected to the distal end 94 of the shaft over the nominal diameter heating element 92. The larger diameter heating element 100 has a second outer diameter D2 that is greater than the first outer diameter D1. A second treatment location T2 may then be ablated with the larger diameter heating element 100. Alternatively, the larger diameter heating element 100 may be used first, then removed to treat smaller HAS.

In certain embodiments, the method may further comprise detecting with a power source 18 connected to the proximal end of the catheter shaft 90 whether the larger diameter heating element 100 is connected to the catheter shaft 90, and adjusting an energy output to a desired energy output. Detecting whether the larger diameter heating element 100 is connected may comprise measuring at least one of a resistance value and an inductance value of the connected heating element by passing a small current through the connected heating element and determining if the larger diameter heating element 100 is connected based on the result. And in yet further embodiments, the method may comprise disconnecting the larger diameter heating element 100 from the catheter shaft 90 and connecting a third heating element to the shaft, the third heating element having a third diameter that is greater than the second diameter D2.

FIGS. 14A and 14B illustrate one embodiment for detecting a type of catheter and/or heating segment attached to the power source 18 in order to adjust the power output from the power source 18 to achieve a desired treatment outcome. This embodiment provides a multi-pin connector 119 (FIG. 14A) in the handle 16 and a chip 21 (FIG. 14B) that connects to the multi-pin connector 119. The chip 21 stores information about the catheter and/or heating segment 15. When the handle 16 is connected to the power source 18, the power source 18 reads the information stored on the chip and adjusts power output accordingly. Information stored on the chip 21 may include, for example, control parameters, treatment time, and catheter type information.

The chip 21 may be, for example, an off-the-shelf EPROM-type chip, such as DS2502+. With reference to FIG. 14B, the chip 21 has at least three pins, including a signal ground pin 23, a communication signal pin 25, and a non-functional pin 27. The functional pins 23, 25 are connected to two pins 29, 31 of the multi-pin connector 119 of FIG. 14A for data communication. The remaining pins of the multi-pin connector 119 may be connected to various other components. For example, two of the pins 33, 35, may be connected to the heating segment 15 for energy delivery, two of the pins 37, 39, may be connected to a temperature sensor on or adjacent the heating segment 15 for temperature feedback, and two of the pins 41, 43, may be connected to a light source at or adjacent the distal end 13 of the shaft 12 for external visualization.

As described above, the present embodiments advantageously provide treatment devices having a heating element with a selectable length or diameter. These embodiments enable the length or diameter of the heating element to be changed on the fly during a treatment procedure, without a need to interrupt the procedure or provide a complete second treatment device. Thus a single catheter may be used at different locations in the HAS by using a shorter heating segment for shorter HAS (such as the STV and some of the SSV) and a longer heating segment for longer HAS (such as the GSV and some of the SSV), a larger diameter heating segment for larger veins (such as the GSV and some of the SSV), and a smaller diameter heating segment for smaller veins (such as some of the SSV and STV), thus achieving greater efficiency during treatment, faster procedure time and better patient outcomes. In addition, these embodiments may include an "intelligent" power source that is able to automatically detect the length or diameter of the heating segment and adjust power delivery for a desired energy output, further enhancing efficiency during treatment and achieving better patient outcomes.

In any of the present embodiments, the treatment devices may be included in a kit that includes the catheter shaft and handle, together with any of the heating elements or heating assemblies. The power source and cable may be provided separately from the kit. Alternatively, the kit may also include a cable attached to the handle. The kit may then be sealed and sterilized. For example, the kit may be sterilized by a procedure performed with ethylene oxide (EtO).

Further, in certain embodiments the system may leverage reprocessing concepts, in that the heating element may be disposable for single use to maintain safety and sterility, while the remaining components, such as the catheter, power source, handle, and cable, can be cleaned and reused. Reuse of the catheter shaft should reduce operation costs passed on to the patient. The patient incurs only the cost of the new heating elements or heating assemblies, and not the cost of a new catheter shaft and handle. Specifically, in one embodiment, the heating elements or heating assemblies are discarded after a single use. Thereafter, the catheter shaft and handle is collected and cleaned. Following cleaning, the used catheter shaft and handle may be repackaged into a kit with new heating elements or heating assemblies, sealed and sterilized. For example, the kit containing the cleaned, used catheter shaft and handle, and new heating elements or heating assemblies is subjected to a sterilization process using EtO.

In any of the present embodiments, during operation, the power delivered to the heating element may be automatically adjusted by the power supply based on a feedback loop. The feedback parameters may be, for example, temperature at the treatment site, or inductance/resistance values at the treatment site. Such automatic power adjustment facilitates achieving an effective temperature for vessel ablation.

It is to be understood that the foregoing description is intended to illustrate and not limit the scope of the invention, which is defined by the scope of the appended claims. Other embodiments are within the scope of the following claims.

What is claimed is:

1. A tissue treatment device, comprising:
   a power source;
   an elongate shaft having a distal end;
   a heating element disposed at the distal end of the shaft, the heating element having a proximal end and a distal end;
   a first electrical pathway configured to extend between the power source, the proximal end of the heating element, and the distal end of the heating element, and defining a first treatment length extending between the proximal and distal ends of the heating element;
   a second electrical pathway configured to extend between the power source, the distal end of the heating element, and an intermediate point along the heating element intermediate the proximal and distal ends thereof, and defining a second treatment length extending between the intermediate point and the distal end of the heating element, wherein the intermediate point is offset from a lengthwise center of the heating element; and
   a third electrical pathway configured to extend between the power source, the proximal end of the heating element, and the intermediate point along the heating element, and defining a third treatment length extending between the intermediate point and the proximal end of the heating element, wherein each of the first treatment length, the second treatment length, and the third treatment length is different,
   wherein the power source is configured to automatically determine the treatment length of the electrical pathway to which the power source is electrically connected and adjust a level of power delivery for a desired energy output based on the treatment length of the electrical pathway to which the power source is electrically connected.

2. The tissue treatment device of claim 1, further comprising a switch configured for selection of power delivery to the first electrical pathway, the second electrical pathway, or the third electrical pathway.

3. The tissue treatment device of claim 1, wherein the heating element is an electrically resistive heating element.

4. The tissue treatment device of claim 3, wherein the heating element is an electrically resistive coil.

5. A tissue treatment device, comprising:
   an elongate shaft having a distal end;
   a heating element disposed at the distal end of the shaft, the heating element having a proximal end and a distal end;
   a power source;
   a first electrical pathway configured to extend between the power source, the proximal end of the heating element, and the distal end of the heating element, and defining a first treatment length extending between the proximal and distal ends of the heating element;
   a second electrical pathway configured to extend between the power source, the distal end of the heating element, and an intermediate point along the heating element between the proximal and distal ends thereof, and defining a second treatment length extending between the intermediate point and the distal end of the heating element, wherein the intermediate point is offset from a lengthwise center of the heating element; and
   a third electrical pathway configured to extend between the power source, the proximal end of the heating element, and the intermediate point along the heating element, and defining a third treatment length extending between the intermediate point and the proximal end of the heating element, wherein each of the first treatment length, the second treatment length, and the third treatment length is different,
   wherein the power source is configured to automatically determine the treatment length of the electrical pathway to which the power source is electrically connected based on at least one of an impedance value of the heating element or a strength of a magnetic field generated when the heating element is energized, and adjust a level of power delivery for a desired energy output based on the electrical pathway to which the power source is electrically connected.

6. The tissue treatment device of claim 5, further comprising a switch configured for selection of power delivery to the first electrical pathway, the second electrical pathway, or the third electrical pathway.

7. The tissue treatment device of claim 5, wherein the heating element is an electrically resistive heating element.

8. The tissue treatment device of claim 7, wherein the heating element is an electrically resistive coil.

* * * * *